United States Patent
Banov

(10) Patent No.: US 9,913,807 B2
(45) Date of Patent: *Mar. 13, 2018

(54) TOPICAL PHARMACEUTICAL BASES FOR TREATING SKIN CONDITIONS

(71) Applicant: Professional Compounding Centers of America (PCCA), Houston, TX (US)

(72) Inventor: Daniel Banov, Sugar Land, TX (US)

(73) Assignee: Professional Compounding Centers of America, Houston, TX (US)

(*) Notice: Subject to any disclaimer, the term of this patent is extended or adjusted under 35 U.S.C. 154(b) by 174 days.

This patent is subject to a terminal disclaimer.

(21) Appl. No.: 14/831,137

(22) Filed: Aug. 20, 2015

(65) Prior Publication Data

US 2016/0051610 A1  Feb. 25, 2016

Related U.S. Application Data

(60) Provisional application No. 62/039,790, filed on Aug. 20, 2014.

(51) Int. Cl.
| | |
|---|---|
| *A61K 36/00* | (2006.01) |
| *A61K 31/015* | (2006.01) |
| *A61K 36/32* | (2006.01) |
| *A61K 45/06* | (2006.01) |
| *A61K 9/00* | (2006.01) |
| *A61K 36/47* | (2006.01) |
| *A61K 47/14* | (2017.01) |
| *A61K 47/44* | (2017.01) |

(52) U.S. Cl.
CPC .......... *A61K 31/015* (2013.01); *A61K 9/0014* (2013.01); *A61K 36/32* (2013.01); *A61K 36/47* (2013.01); *A61K 45/06* (2013.01); *A61K 47/14* (2013.01); *A61K 47/44* (2013.01)

(58) Field of Classification Search
CPC ...................................................... A61K 36/00
See application file for complete search history.

(56) References Cited

U.S. PATENT DOCUMENTS

2010/0284943 A1* 11/2010 Frota Correa ......... A01N 65/00
  424/47
2012/0202882 A1*  8/2012 Banov ...................... A61K 9/00
  514/570

* cited by examiner

*Primary Examiner* — Qiuwen Mi
(74) *Attorney, Agent, or Firm* — David G. Woodral; Scott R. Zingerman; Gable Gotwals

(57) ABSTRACT

The present disclosure refers to topical pharmaceutical bases that possess scar healing properties. Further, these topical pharmaceutical bases are proposed for treating skin conditions, such as, for example keloids, hypertrophic scars, wounds, and burns, among others. The topical pharmaceutical bases include Amazonian oils and resins, such as pracaxi oil and breu-branco resin. The synergistic effect of pracaxi oil combined with breu-branco resin results in a highly effective scar and wound treatment. Suitable active pharmaceutical ingredients (APIs) can be incorporated to the topical pharmaceutical bases to formulate topical pharmaceutical compositions, which improve healing effects. The synergistic effect provided by the combination of pracaxi oil and breu-branco resin enables lower dosage requirements of the associated APIs when topical pharmaceutical compositions are employed for treating skin conditions.

9 Claims, No Drawings

TOPICAL PHARMACEUTICAL BASES FOR TREATING SKIN CONDITIONS

CROSS-REFERENCE TO RELATED APPLICATIONS

This application claims priority to U.S. Provisional Application Ser. No. 62/039,790, filed Aug. 20, 2014, which is hereby incorporated by reference.

BACKGROUND

Field of the Disclosure

The present disclosure relates generally to pharmaceutical compositions, and more particularly, to topical pharmaceutical bases including natural components for treating skin conditions.

Background Information

Typically, a healed wound produces a scar. A scar is growth of collagen beneath the skin that is formed as the result of wound healing; therefore, every cut or injury to the skin heals to form a scar. Proper wound healing results in an invisible scar. Early in the process, scars are red or dark and raised, but become paler and flatter over time. While a visible scar is the necessary and inevitable end to the healing process, the results vary with the individual, the type of injury, and time, among others. For example, when scars are over about two months old to about two years old, scars tend to become harder to treat, and after two years a surgery is necessary to remove the scars, which results in new scars appearing after the removal surgery.

Additionally, excessive scarring results from an imbalance in the anabolic and catabolic wound healing processes. In the formation of an abnormal scar, more collagen is produced than is degraded. Therefore, the scar grows larger than is required for wound healing, with an over-production of cells, collagen, and proteoglycan. Scars resulting from excessive scarring or the abnormalities in wound healing include fibrosis, fibromatosis, keloidosis, adhesions (e.g., surgical adhesions), hypertrophic scars, fibrocystic conditions, and joint stiffness. For example, keloids grow in all directions, become elevated above the skin, and remain hyperemic. The exact mechanisms of excessive scarring are poorly understood, but it is believed that common mechanisms underlie the formation of both keloids and hypertrophic scars. Further, research results suggest that increased transforming growth factor β (TGF-β) expression plays a role in excessive scarring, due to promoting extracellular matrix production, and because of being produced at elevated levels by keloid fibroblasts and hypertrophic scars. Abnormal scars or abnormalities in wound healing are also categorized into various conditions based on the type of tissue in which a wound occurs. Abnormal scar formation in skin may lead to, for example, keloid, hypertrophic scar, contracture, or scleroderma.

Generally, methods for treating scars and keloids have a low success probability and are costly and complicated. For example, treatment of keloids and hypertrophic scars has included surgical excision followed by graft application, with a risk of new scars being developed after the excisions. Pressure has also been used to cause scar thinning; for example, pressure bandages placed over scars have resulted in some scar thinning, but a pressure of at least 25 mm Hg needs to be maintained constantly for approximately six months in usual situations for any visually observable effect. Ionizing radiation therapy has also been employed. Other treatments include application of silicone pads to the scar tissue surface, sometimes under pressure provided by an elastomeric bandage; topical application of silicone gel sheets, with or without added vitamin E; and topical or intra-lesional treatment with corticosteroids.

Therefore, there is a need for improved pharmaceutical formulations and methods for treating skin conditions.

SUMMARY

The present disclosure refers to topical pharmaceutical bases that possess scar healing properties. Further, these topical pharmaceutical bases are proposed for treating skin conditions. In some embodiments, skin conditions include keloids, hypertrophic scars, wounds, and burns, among others.

In some embodiments, the topical pharmaceutical bases include natural components from the Amazon forest. In these embodiments, the topical pharmaceutical bases include pracaxi oil and breu-branco resin. Further to these embodiments, aforementioned natural components exhibit moisturizing, antimicrobial, and healing properties.

In an example, the topical pharmaceutical bases include: pracaxi oil in a concentration from about 0.5% w/w to 20% w/w, preferably from about 5% to 10% w/w; and breu-branco in a concentration from about 0.5% w/w to 20% w/w, preferably from about 5% w/w to 10% w/w.

In other embodiments, the topical pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. Further to these embodiments, the concentration of each natural component within topical pharmaceutical bases is from about 1% w/w to 20% w/w, more preferably about 5% w/w.

In some embodiments, the topical pharmaceutical bases are in a dosage form selected from the group consisting of: pharmaceutically acceptable liquids, creams, oils, lotions, ointments, gels, roll-on liquids, skin patches, sprays, glass bead wound dressings, and synthetic polymer dressings, among others.

In some embodiments, the topical pharmaceutical bases are directly administered onto the affected area. In these embodiments, suitable applicators are employed to administer the topical pharmaceutical bases. In an example, suitable applicators include a swab, brush, cloth, pad, and sponge, among others.

In some embodiments, when the topical pharmaceutical bases are applied onto the affected area, the topical pharmaceutical bases deliver a therapeutically effective amount of fatty acids including behenic acid, triterpenes α, β amyrins, and other aforementioned components, which help in the treatment of wounds and scars. In these embodiments, the synergistic effect of pracaxi oil combined with breu-branco resin within the topical pharmaceutical bases results in a highly effective healing topical formulation, especially for wounds and excessive scarring.

In other embodiments, active pharmaceutical ingredients (APIs) are incorporated into the topical pharmaceutical bases to formulate topical pharmaceutical compositions. In these embodiments, the synergistic effect of the combination of pracaxi oil and breu-branco resin enables lower dosage requirements of the associated APIs when topical pharmaceutical compositions are employed for treating skin conditions.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

Numerous other aspects, features, and benefits of the present disclosure may be made apparent from the following detailed description.

DETAILED DESCRIPTION

The present disclosure is here described in detail with reference to embodiments. Other embodiments may be used and/or other changes may be made without departing from the spirit or scope of the present disclosure. The illustrative embodiments described in the detailed description are not meant to be limiting of the subject matter presented herein.

Definitions

As used here, the following terms have the following definitions:

"Abnormal scar" refers to the over-expression of collagen at a wound site or in a scar, leaving an unaesthetic mark. Abnormal scars may include keloids and hypertrophic scars, among others.

"Active Pharmaceutical Ingredients (APIs)" refer to chemical compounds that induce a desired effect, and include agents that are therapeutically effective, prophylactically effective, or cosmeceutical effective.

"Excessive scarring" refers to a process that result from an imbalance in the anabolic and catabolic wound healing processes, causing overgrowth of dense fibrous tissue and which bring about one or more abnormal scars. Excessive scarring is characterized by overproduction of cells, collagen, and/or proteoglycan.

"Hypertrophic scars" refer to abnormal scars in which dense fibrous tissue does not extend beyond borders of an original wound or incision, and which tend to be wider than necessary for normal wound healing to occur.

"Keloids" refer to abnormal scars resulting from benign fibrous growths that occur after trauma or wounding of the skin, which extend beyond original areas of skin injury, and which tend to remain elevated.

"Oil" refers to a vegetable substance that may be clear, odorless, viscous, hydrophobic, liquid or liquefiable at room temperature. Oils are widely used in cosmetics due to its hypoallergenic and non-comedogenic properties.

"Patient" refers to warm-blooded animals, such as mammals, for example, humans, who are in need of treatment.

"Resin" refers to a hydrocarbon secretion of many plants, which possesses valuable chemical properties.

"Therapeutically effective amount" refers to the amount of subject compound that will elicit the biological or medical response of a tissue, system, animal or human that is being sought.

"Treating" and "Treatment" refers to reduction in severity and/or frequency of symptoms, elimination of symptoms and/or underlying cause, prevention of the occurrence of symptoms and/or their underlying cause, and improvement or remediation of damage.

DESCRIPTION OF THE DISCLOSURE

The present disclosure refers to topical pharmaceutical bases that possess scar healing properties. Further, these topical pharmaceutical bases are proposed for treating skin conditions. In some embodiments, skin conditions include keloids, hypertrophic scars, wounds, and burns, among others.

Formulation

In some embodiments, the topical pharmaceutical bases include natural components from the Amazon forest. In these embodiments, the topical pharmaceutical bases include pracaxi oil and breu-branco resin. Further to these embodiments, aforementioned natural components exhibit moisturizing, antimicrobial, and healing properties.

In an example, the topical pharmaceutical bases include: pracaxi oil in a concentration from about 1% w/w to 20% w/w, preferably from about 5% to 10% w/w; and breu-branco in a concentration from about 1% w/w to 20% w/w, preferably from about 5% w/w to 10% w/w.

Pracaxi Oil

Pracaxi oil is obtained from the seed oil of the *Pentaclethara macroloba* tree, or pracaxi tree. The pracaxi tree is a deciduous tree from the legumes family, growing in altitudes below 600 meters in many parts of northern Brazil, Guyana, Trinidad, and parts of Central America, and may reach between about 8 and about 35 meters in height. Pracaxi trees may sometimes be found in wetlands, and are resistant to water logging.

Pracaxi seeds include from about 45% to 48% fat, about 27% to 28% protein, and about 12% to 14% carbohydrates (see Table 1). Pracaxi seed oil includes the highest known natural concentration of behenic acid (about 20%) in a vegetable fat, more than six times higher than in peanut oil, and also includes about 35% of oleic acid. In some cases, pracaxi seed oil may include greater percentages of the aforementioned behenic acid and oleic acid. The oleic acid and lauric acid, contained within pracaxi oil are effective vehicles for delivering drugs through the skin.

TABLE 1

General composition of pracaxi oil.

| Components | Composition % |
|---|---|
| Fat | 45-48 |
| Protein | 27-28 |
| Carbohydrates | 12-14 |

In an example, the fatty acid composition of the pracaxi oil is illustrated below in Table 2. Compositions vary depending on the region and conditions in which the pracaxi tree grows.

TABLE 2

Fatty acid composition of the pracaxi oil.

| Fatty Acids | Carbon Atoms | Composition % |
|---|---|---|
| Lauric | 12:00 | 1.30 |
| Myristic | 14:00 | 1.21 |
| Palmitic | 16:00 | 2.04 |
| Stearic | 18:00 | 2.14 |
| Oleic | 18:10 | 44.32 |
| Linoleic | 18:20 | 1.96 |
| Linolenic | 18:30 | 2.31 |
| Behenic | 22:00 | 9.67 |
| Lignoceric | 24:00 | 14.81 |

TABLE 3

Specifications of the pracaxi oil.

| Indicators | Reference Value |
|---|---|
| Texture | Solid below 18.5° C., liquid viscous texture above this temperature |
| Color | Translucent yellow, yellowish-white when solid |
| Odor | Almost odorless |
| Melting point | 18.5° C. |
| Refractive index (40° C.) | 1.4690 |
| Iodine value | 65-70 g I2/100 g |
| Saponification value | 170-180 mg kOH/g |
| Acid value | 3-5 mg KOH/g |
| Peroxide value | 5-10 mEQ/kg |
| Density (25°) | 0.917 g/cm$^3$ |

Pracaxi oil has been widely employed within pharmaceutical compositions because of its cosmetic, therapeutic, and medicinal properties. Pracaxi oil is rich in organic acids with antioxidant, antibacterial, antiviral, antiseptic, antifungal, anti-parasitic, and anti-hemorrhagic properties. Because pracaxi oil possesses many of the aforementioned properties, pracaxi oil can be suitable oil for helping in the treatment of wounds and scars.

Pracaxi oil has a high amount of solid matter, not fatty acids, which makes pracaxi oil solidifies in cooler temperatures. The solid matter has gentle moisturizing and high cellular renewal promoting properties. It includes vitamin E, and has essential fatty acids, which makes pracaxi oil suitable for topical pharmaceutical compositions.

Breu-Branco Resin

Breu-branco resin (*Protium heptaphyllum, Burseraceae*) is extracted from an Amazon jungle tree called Almécega. Almécega is a tree that grows in dry forests and is native to most of Brazil. The Almécega trees give off an aromatic fragrance and have a dark red bark. Additionally, Almécega trees grow from about 10 to 20 meters in height, and from about 50 to 60 centimeters in diameter at the base.

When a cut is made in the trunk of Almécega trees, the breu-branco resin exudes. This resin has a white-green color and a very pleasant fragrant aroma. Additionally, the breu-branco resin hardens when coming in contact with air. In several areas of Brazil, the resin is collected from the trunk of Almécega trees, and then ground manually after it hardens. Typically, breu-branco resin is collected year round, but especially in the summer season. After the resin is collected, the resin is dried in the shade and then stored in sacks made of fibers, such as jute. Cuts on an Almécega tree to extract the resin are first made when the tree is about 8 to 10 years old. To harvest the resin of this species sustainably, it is recommended that each Almécega tree receives only about 2 to about 3 cuts per year.

Additionally, yields vary according to the process of extraction. For example, the process of hydro-distillation yields about 11% resin, whereas steam distillation yields about 2.5% resin. The general composition of the resin of breu-branco is provided in Table 4, while the monoterpene composition within the resin of breu-branco is provided in Table 5.

TABLE 4

Composition of Breu-Branco Resin.

| Ingredients | Composition % |
|---|---|
| Resinic acids | 60-75 |
| Terpenes | 10-15 |
| Various substances/water | 5-10 |

TABLE 5

Composition of Breu-Branco Resin Monoterpene.

| Monoterpenes | Composition % |
|---|---|
| α-pyrene | 10.50 |
| Limonene | 16.90 |
| α-phellandrene | 16.70 |
| Terpinolene | 28.50 |
| Others | 27.40 |

Breu-branco resin is often used in Amazonian regions for treating some physical conditions. Breu-branco resin is aromatic and rich in triterpenes α, β amyrins, which possess analgesic and anti-inflammatory properties. In traditional medicine, the resin of breu-branco is suggested for asthma, bronchitis, coughs, headaches stomach aches, liver disorders, memory loss, concentration, motor coordination, for soothing states of agitation and stress, as an anti-inflammatory and analgesic, for wound healing, and as a stimulating agent, among others. Due to breu-branco resin's aromatic properties, it is widely used in perfumes and toiletries as well as in soap manufacturing.

In other embodiments, the topical pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. Further to these embodiments, the concentration of each natural component within topical pharmaceutical bases is from about 1% w/w to 20% w/w, preferably about 5% w/w.

In further embodiments, active pharmaceutical ingredients (APIs) are incorporated into the topical pharmaceutical bases to formulate topical pharmaceutical compositions. In these embodiments, the topical pharmaceutical compositions are proposed for treating skin conditions, such as, for example keloids, hypertrophic scars, wounds, and burns, among others.

Administration

In some embodiments, the topical pharmaceutical bases are in a dosage form selected from the group consisting of: pharmaceutically acceptable liquids, creams, oils, lotions, ointments, gels, roll-on liquids, skin patches, sprays, glass bead wound dressings, and synthetic polymer dressings, among others.

In some embodiments, the topical pharmaceutical bases are directly administered onto the affected area. In these embodiments, suitable applicators are employed to administer the topical pharmaceutical bases. In an example, suitable applicators include a swab, brush, cloth, pad, and sponge, among others.

In some embodiments, when the topical pharmaceutical bases are applied onto the affected area, the topical pharmaceutical bases deliver a therapeutically effective amount of fatty acids including behenic acid, triterpenes α, β amyrins, and other aforementioned components, which help in the treatment of wounds and scars. In these embodiments, the synergistic effect of pracaxi oil combined with breu-branco resin within the topical pharmaceutical bases results in a highly effective healing topical formulation, especially for wounds and excessive scarring. Further to these embodiments, the synergistic effect of the combination of pracaxi oil and breu-branco resin enables lower dosage requirements of the associated APIs when topical pharmaceutical compositions are employed for treating skin conditions.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A topical pharmaceutical composition comprising:
about 1% w/w to about 95% w/w pracaxi oil,
a synergistically effective amount of breu-branco resin, and
a pharmaceutically effective amount of at least one active pharmaceutical ingredient.

2. The topical pharmaceutical composition of claim 1, wherein the topical pharmaceutical composition comprises about 5% w/w to about 50% w/w breu-branco resin.

3. The topical pharmaceutical composition of claim 2, wherein the topical pharmaceutical composition comprises about 10% w/w to about 20% w/w pracaxi oil.

4. The topical pharmaceutical composition of claim 2, wherein the topical pharmaceutical composition comprises about 10% w/w breu-branco resin.

5. The topical pharmaceutical composition of claim 1, wherein the topical pharmaceutical composition further comprises at least one natural component selected from the group consisting of buriti oil, copaiba balsam, bacaba oil, acai oil, ojon oil, andiroba oil, murumuru butter, and tucuma oil.

6. The topical pharmaceutical composition of claim 1, wherein the topical pharmaceutical composition further comprises at least one natural component selected from the group consisting of about 1% w/w to about 20% w/w buriti oil, about 1% w/w to about 20% w/w copaiba balsam, about 1% w/w to about 20% w/w bacaba oil, about 1% w/w to about 20% w/w acai oil, about 1% w/w to about 20% w/w ojon oil, about 1% w/w to about 20% w/w andiroba oil, about 1% w/w to about 20% w/w murumuru butter, and about 1% w/w to about 20% w/w tucuma oil.

7. The topical pharmaceutical composition of claim 3, wherein the topical pharmaceutical composition further comprises at least one natural component selected from the group consisting of about 1% w/w to about 20% w/w buriti oil, about 1% w/w to about 20% w/w copaiba balsam, about 1% w/w to about 20% w/w bacaba oil, about 1% w/w to about 20% w/w acai oil, about 1% w/w to about 20% w/w ojon oil, about 1% w/w to about 20% w/w andiroba oil, about 1% w/w to about 20% w/w murumuru butter, and about 1% w/w to about 20% w/w tucuma oil.

8. The topical pharmaceutical composition of claim 1, wherein the topical pharmaceutical composition further comprises at least one natural component selected from the group consisting of about 5% w/w buriti oil, about 5% w/w copaiba balsam, about 5% w/w bacaba oil, about 5% w/w acai oil, about 5% w/w ojon oil, about 5% w/w andiroba oil, about 5% w/w murumuru butter, and about 5% w/w tucuma oil.

9. The topical pharmaceutical composition of claim 1, wherein the topical pharmaceutical composition is selected from the group consisting of a pharmaceutically acceptable liquid, a cream, an oil, a lotion, an ointment, a gel, a roll-on liquid, a skin patch, a spray, and a synthetic polymer dressing.

* * * * *